United States Patent [19]

Meier et al.

[11] Patent Number: 5,158,457
[45] Date of Patent: Oct. 27, 1992

[54] DENTAL PROCESS AND INSTRUMENT FOR POLISHING ROOTS OF TEETH

[76] Inventors: Peter Meier, Alte Birmensdorfestrasse 1, Fislisbach; Andre Schwander, Mühlbergweg 25 D, Baden, both of Switzerland; Ludwig Römhild, Am Kugelfeld 3, Berchtesgaden, Fed. Rep. of Germany

[21] Appl. No.: 409,670

[22] Filed: Sep. 20, 1989

[30] Foreign Application Priority Data

Sep. 20, 1988 [CH] Switzerland .................. 3495/88

[51] Int. Cl.⁵ .................................. A61C 1/07
[52] U.S. Cl. ...................... 433/121; 433/122; 433/118
[58] Field of Search ............... 433/118, 121, 125, 122

[56] References Cited

U.S. PATENT DOCUMENTS

| | | | |
|---|---|---|---|
| 4,289,486 | 9/1981 | Sargeant | 433/118 |
| 4,341,519 | 7/1982 | Kuhn et al. | 433/121 X |
| 4,353,696 | 10/1982 | Bridges | 433/125 |
| 4,731,019 | 3/1988 | Martin | 433/125 X |
| 4,820,153 | 4/1989 | Romhild et al. | 433/118 |

FOREIGN PATENT DOCUMENTS

| | | | |
|---|---|---|---|
| 3320211 | 12/1984 | Fed. Rep. of Germany | 433/118 |
| 155090 | 12/1920 | United Kingdom | 433/118 |

Primary Examiner—Robert P. Swiatek
Assistant Examiner—Nicholas D. Lucchesi
Attorney, Agent, or Firm—EGLI International

[57] ABSTRACT

A polishing dental instrument includes a polisher, which is vibrated by a drive shaft connected to a motor-driven drive via an eccentric pin. The eccentric movements are elastically transferred to two arms via two compression springs. The arms are fixed to a displaceably guided bearing sleeve positioned in a casing. The polisher which is guided in the bearing has an end piece whose lateral edges are adapted to smooth or clean the tooth root surface. As a result of the elastically transferred reciprocating movements of the eccentric pin a very fine smoothing of the root surface is obtained.

12 Claims, 3 Drawing Sheets

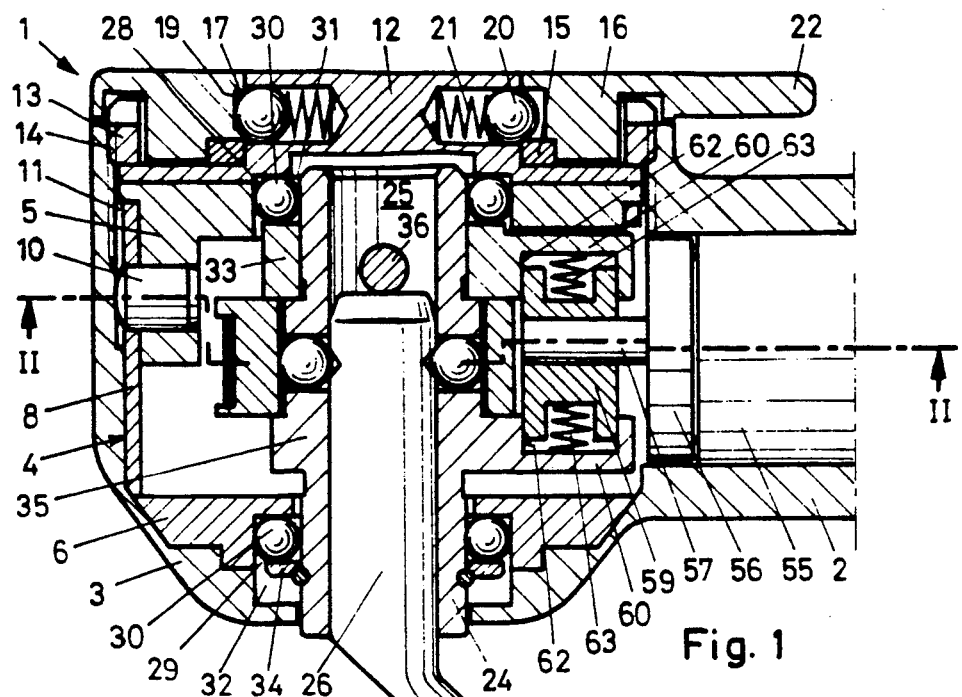
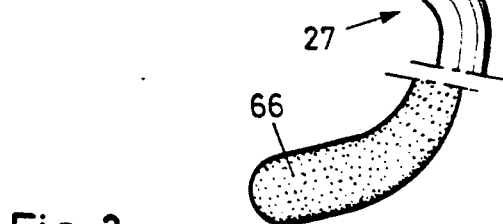
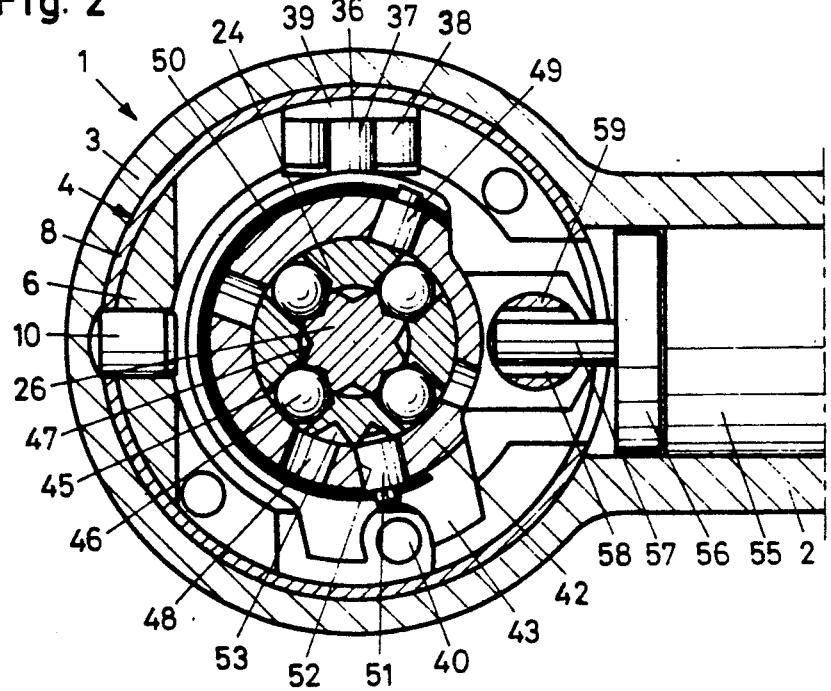

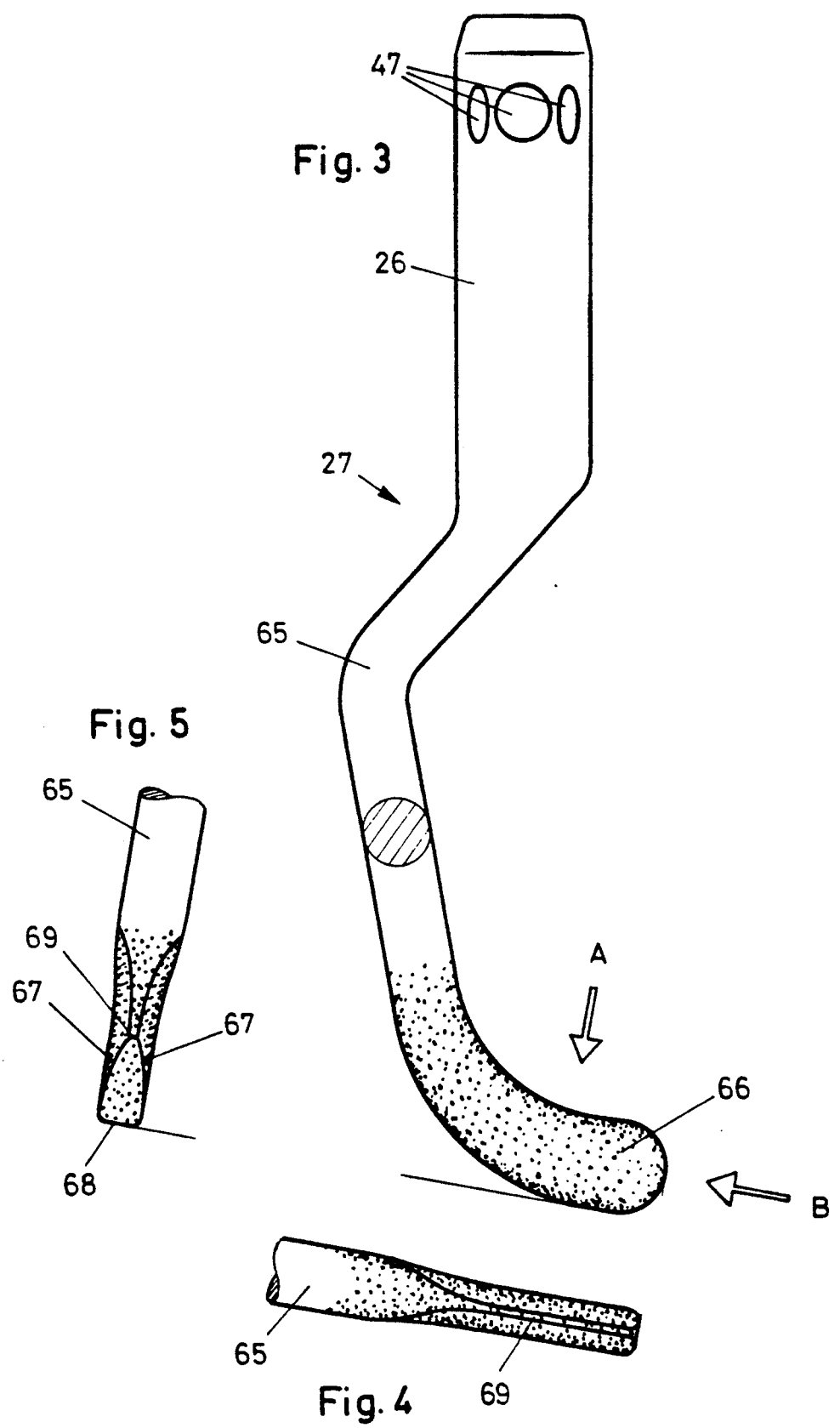

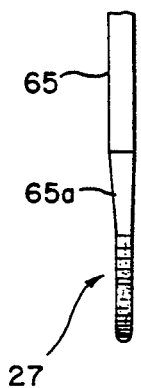
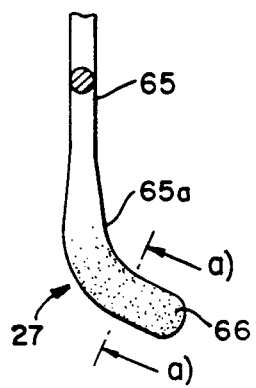
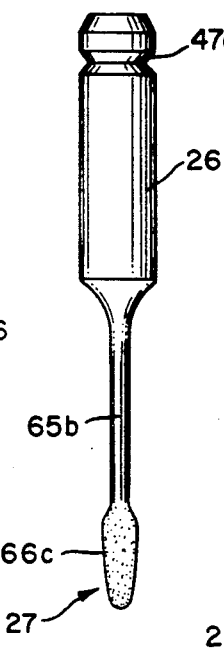
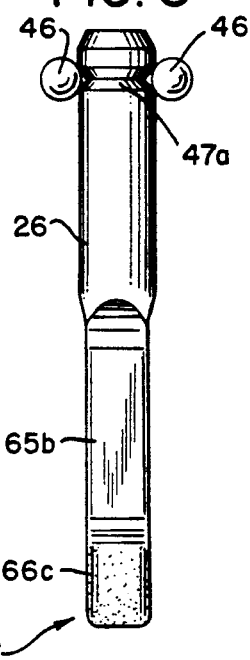
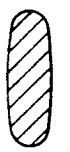
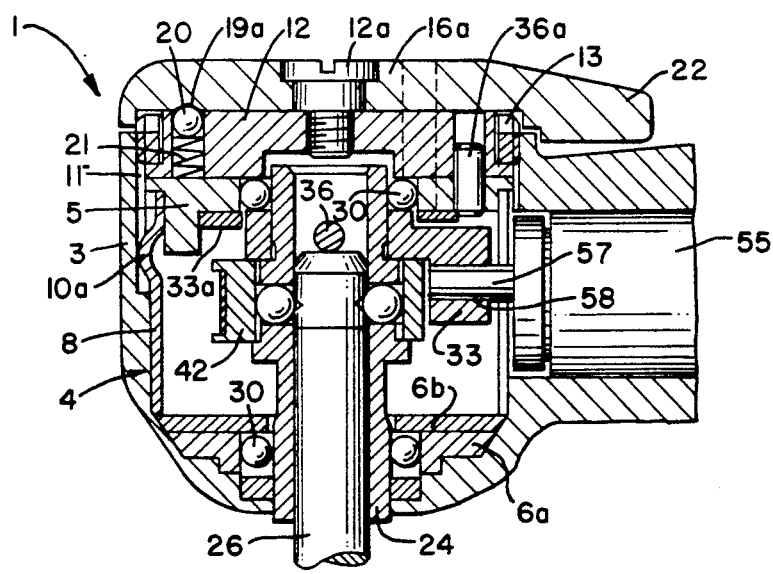

DENTAL PROCESS AND INSTRUMENT FOR POLISHING ROOTS OF TEETH

BACKGROUND OF THE INVENTION

The present invention relates to a process for treating a tooth, and in particular its root parts located under the gums with the aid of a dental instrument, having a scraping tool provided with a drive incorporated into the instrument handle for imparting to the tool a reciprocating movement, as well as to a dental instrument for performing the process.

Apart from the hand-operated instruments used for the odontopathy treatment, particularly periodontosis and which are referred to as scalers, use is also made of scalers, which are equipped with a motor drive and in which a reciprocating movement is imparted to the scraping means or curette located at the end of the handle. The motordriven instruments make the work of the dentist or surgeon much easier to do as compared with hand-operated instruments. The scraping curette, with the edge of which the tooth is cleaned, is moved along the root of the tooth under the gums, and under pressure it is suddenly moved in the direction of the tooth masticatory surface.

The motor-driven scaler has proved to be satisfactory in operation, because it is possible to efficiently treat the surface parts of the tooth root, so that on the root surfaces are formed smooth, clean and slightly concave surface portions.

Recent research has revealed that it is desired to smooth these minor depressions. The known instruments cannot be used for such smoothing purposes and consequently hand-operated instruments have to be used.

SUMMARY OF THE INVENTION

It is an object of the present invention to provide an improved process of the aforementioned type, which is suitable for the polishing or smoothing-out of the tooth root.

This and other objects of the invention are attained by a process, in which the tooth root surface is smoothed by means of a polishing tool or polisher, smoothing being carried out by the edges or sides of the polisher through the reciprocating movement thereof. Appropriately, the reciprocating polishing movement is imparted to the polisher by the drive via a flexible clutch and, preferably, the polisher performs a harmonic oscillation or vibration.

The invention also covers a dental instrument, the function of which is to permit the performance of the process in an optimal manner.

The afore-described objects are further attained by a dental instrument, having a drive for imparting a reciprocating movement to a polisher which is displaceably guided by means of a bearing sleeve in a casing of the dental instrument, in which two arms are provided, which are operatively connected to an eccentric drive driven by the drive.

In an embodiment, the eccentric drive includes an eccentric pin connected to a drive shaft of the drive, a lifting bolt having a slot receiving the eccentric pin, and two arms supported on the bearing sleeve, the lifting bolt being displaceably guided in the arms.

In another embodiment, the slot for receiving the eccentric pin is provided in a thrust ring fixed to the bearing sleeve.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

FIG. 1 is a longitudinal section through a polishing instrument according to a first embodiment of the present invention;

FIG. 2 is a section along line II—II of FIG. 1;

FIG. 3 is a side view of a polisher of the instrument of FIG. 1;

FIG. 4 is a view of the end piece of the polisher according to FIG. 3 from arrow direction A;

FIG. 5 is a view of the end piece of the polisher according to FIG. 3 from arrow direction B;

FIG. 6 is a side view of another embodiment of the polisher;

FIG. 6a is a cross-section taken along lines a—a of FIG. 6;

FIG. 7 is a front view of the polisher of FIG. 6;

FIG. 8 is a side view of yet another embodiment of the polisher;

FIG. 9 is a front view of the polisher of FIG. 8; and

FIG. 10 is a longitudinal section through a polishing instrument according to a second embodiment of the invention.

DETAILED DESCRIPTION OF THE PREFERRED EMBODIMENT

The polishing instrument shown in FIG. 1 comprises a casing constructed as an angle piece and which includes an only partly shown handle casing 2 and a tool outer casing 3. A motor for driving the polisher is housed in a known manner in the handle casing 2. However, it is also possible to couple the handle casing with a flexible shaft of the main drive of a dental instrument, so that in such case the polishing instrument 1 would not require its own drive. An inner casing 4 is placed in the tool outer casing 3. The inner casing 4 includes an upper bearing web 5, a lower bearing web 6 and an interposed thrust ring 8. A guide bolt 10 links the bearing web 5 and thrust ring and projects into a guide groove formed in the inner wall of the tool casing 3. Thus, the inner casing 4 is positioned relative to the tool outer casing 3.

On the upper bearing web 5, is mounted a cover 12, which is fixed together with the inner casing 4 by a ring nut 13 screwed into an internal thread 14 provided in the inner wall of tool outer casing 3. A ball holding ring 15 is inserted in cover 12.

The cover 12 is surrounded by a control ring 16 having a bore 17. A radial groove is formed in bore 17, in which are engaged by means of springs 21 locking members 20, e.g. balls for holding or retaining the control ring 16. For positioning the control ring 16, there are formed two positioning recesses 19 (one of these being visible in FIG. 1) for engaging one of the locking members 20. Control ring 16 is provided with adjusting means for its adjustment, e.g. a lever 22 or a knurled edge.

A bearing sleeve 24 is mounted in inner casing 4. Bearing sleeve 24 has a bore 25 for receiving a shank 26 of a polishing tool or polisher 27. Bearing sleeve 24 is axially displaceably guided in bearings 28, 29. Bearings 28, 29 are roller bearings with roller balls 30, which are located in recesses 31, 32 of inner casing 4. The recess 31 of the upper bearing 28 is bounded by the cover 12 and a thrust ring 33, whilst recess 32 of the lower bearing 29 is bounded by the lower bearing web 6 and a thrust ring 34 supported on the bearing sleeve 24. The latter has a larger diameter or wall thickness portion 35 located between the bearings 28, 29 and via which a securing pin 36 extends diagonally through the sleeve 24, which carries on its one end 37 a roller bearing 38, which is guided in a slot 39 of the upper bearing web 5. Rotation of the bearing sleeve 24 is prevented by the securing pin 36 in slot 39, cf. FIG. 2.

FIG. 2 shows a driving pin 40 fixed in control ring 16 and which projects into the vicinity of the larger diameter portion 35 of bearing sleeve 24, which is surrounded by a coupling ring 42, which in turn is provided on its outer circumference with a control fork 43, into which projects the driving pin 40.

In the enlarged portion 35 of bearing sleeve 24 are provided four diametrically opposing bores 45, in which are guided coupling members or bodies 46, e.g. balls which, in the position shown in FIG. 2, project into depressions 47 arranged on the outer circumference of shank 26 of polisher 27 and therefore couple the polisher to the bearing sleeve 24. For uncoupling purposes, e.g. for changing or rotating the polisher 27, coupling ring 42 is rotated until the bores 48 diametrically arranged therein are aligned with the bores 45 of bearing sleeve 24. A thrust bolt 49 is held by a circlip 50 in a bore 48 of coupling ring 42. The other end of circlip 50 acts on a positioning bolt 51, which is located in a bore 52 of coupling ring 42 and projects into depressions 53 formed on the outer circumference of bearing sleeve 24.

In the position shown in FIG. 2, the coupling members 46 are blocked in depressions 47 of shank 26. If coupling ring 42 is now turned clockwise until bores 48 come into register or alignment with bores 45, the coupling members 46 are moved into the bores 48, so that the polisher 27 can be replaced, removed or turned into a new position. Positioning bolt 51 is engaged in the adjacent depression 53 in the uncoupled position. Therefore it is possible to maintain the coupling and uncoupling position of coupling ring 42. The coupling ring 42 is moved by rotating the control ring 16, cf. FIG. 1, so that the driving pin 40 rotates the control fork 43 and therefore the coupling ring 42 into the desired position.

A drive shaft 55 is rotatably mounted in handle casing 2 and has on its end an eccentrically positioned pin 57 at the transition of casing 2 on the end face 56. Pin 57 projects into a slot 58 of a lifting bolt 59. Lifting bolt 59 is longitudinally displaceably supported in bores 62 of two arms. One end of a compression spring 63 is in each case supported on the respective end face of the lifting bolt 59, whilst the other end of spring 63 is supported on one of the arms 60. One arm 60 is integrally connected to the thrust ring 33

Upon rotating the drive shaft 55, the eccentric pin 57 brings about reciprocating vibration of lifting bolt 59. This vibration is transferred via compression spring 6 to arms 60 and therefore to bearing sleeve 24. Therefore the polisher 27 receives a reciprocating oscillating movement, which has the same path in both lifting directions, and it is consequently possible to produce the movement suitable for smoothing the root surface. This movement can be influenced by different springs 63.

The polisher 27 shown in FIG. 3 has a shank 26, to which is connected an offset shank part 65, which has a circular cross-section. To the shank part 65 is connected an end piece 66, whose shape can be gathered from FIGS. 4 and 5. According to FIG. 5, it is important that the end piece 66 has two edges or sides 67, which run together in the direction of the tool casing 3. The edges 67 exert the polishing action on the tooth root. On the side remote from the tool casing 3 the profile has a planar face 68. FIGS. 4 66 can also be coated with diamond dust.

The combination of vibrations transferred by the compression springs 63 with the shape of edges 67 provided onto the end piece 66 of polisher 27 leads to an optimal smoothing action.

FIGS. 6 and 7 illustrate another embodiment of the polisher 27 which is substantially similar to that shown in FIG. 3 but differs from the polisher described in connection with FIG. 3 in that it has the end piece 66 rounded at all sides or in both mutually normal cross-sections, as seen in FIGS. 6 and 6a. In this polisher also denoted at 27, the main shank and the offset shank part are constructed identically to the polisher of FIG. 3. The offset shank part 65 having a circular cross-section merges into a transition part 65a, where the shank cross-section assumes an oval shape, followed by the bent end piece 66 which has an elongated cross-section and is rounded along the entire periphery thereof. It is possible with the polisher according to FIGS. 6 and 7, to treat the tooth root parts, particularly in the gaps between the teeth. For this purpose, polisher 27 of FIGS. 6 and 7 has the same depressions 47 in its shank as those in the polisher of FIG. 3, so that the position of the end piece 66 with respect to the casing 1 is fixed.

FIGS. 8 and 9 show yet another embodiment of the polisher 27, the construction of which differs considerably from the embodiments according to FIGS. 3 and 6. In this embodiment, a pear-shaped or spade-shaped end piece 66c is not offset with respect to shank 26 but is coaxial with the latter. Thus, the polisher according to FIGS. 8 and 9 is constructed as a straight rod, in which shank 26 merges into a narrower shank part 65b, to which is integrally connected the end piece 66c having the same lateral expansion as shank part 65b in one cross-section of the polisher.

A further important feature of the polisher 27 according to FIGS. 8 and 9 is that instead of depressions being provided in the upper end of shank 26, there is a fixing groove 47a. This means that the polisher is axially held in the bearing sleeve 24, but can rotate and is therefore self-centering. This polishing tool makes it possible to work in a particularly advantageous manner on the root faces, which are freely accessible. Due to free rotatability of the polisher of this embodiment, the end piece 66c can closely adapt to the root portion, which facilitates polishing. However, this polisher is less suitable for treating root portions between adjacent teeth. The polishers according to FIGS. 3 and 6 can be looked upon as universal polishers, whereas the polisher of FIGS. 8 and 9 is a special polisher.

FIG. 10 shows another embodiment of the tool in which the tool casing 1 formed as an angle piece is simplified. The essential parts of the bearing sleeve 24 and the coupling ring 42 are unchanged as compared with the construction according to FIGS. 1 and 2. The eccentric drive and the upper part of the outer casing are simpler than those in the embodiment of FIGS. 1 and 2. Slot 58 for receiving the eccentric pin 57 is provided in thrust ring 33. However, the springs 63 of the embodiment of FIG. 1 are omitted. Guide bolt 10 is replaced with the radially outwardly extending stamped projection 10a, which is provided on the thrust ring 8 and projects into guide slot 11 formed in the outer casing 3, whilst the upper end of thrust ring 8 secures the upper bearing web 5. The upper bearing web 5 is connected by a connecting pin 36a to cover 12. As in the construction according to FIG. 1, the cover 12 is pressed by the ring 13 onto the thrust ring 8. Unlike in the embodiment of FIGS. 1 and 2, the locking balls 20 with springs 21 are positioned in vertically extending grooves and project into positioning recesses 19a provided on the underside of a switch cover 16a positioned above cover 12 in a sandwich-like manner and provided with lever 22 so that a simplified construction for cover 12 and switch cover 16a is obtained. Switch cover 16a is used for switching the coupling ring 42 and is fitted in rotary manner to cover 12 by a tight-fit screw 12a. A further manufacture simplification is obtained in that the lower ring 6b. Thrust ring 33 is supplemented by an e.g. plastic holding ring 33a, which prevents the roller balls 30 from dropping out. All the other parts of the tool of FIG. 10 are identical to the construction according to FIGS. 1 and 2.

There has been disclosed heretofore the best embodiment of the invention presently contemplated. However, it is to be understood that various changes and modifications may be made thereto without departing from the spirit of the invention.

What is claimed is:

1. Dental instrument for treating a tooth, comprising:
   a motor-driven scraping tool having a polisher for smoothing out the tooth root surface when said tool is reciprocated with essentially harmonic oscillation;
   an outer casing;
   an inner casing placed in said outer casing, said inner casing having an upper bearing web and a lower bearing web and a thrust ring interposed between said webs;
   a bearing sleeve displaceably guided in said thrust ring and receiving said scraping tool;
   a drive incorporated in said outer casing;
   an eccentric drive operatively interconnected between said drive and said bearing sleeve so as to impart reciprocating motion with essentially harmonic oscillation to said scraping tool via said bearing sleeve, said eccentric drive includes an eccentric pin connected to a drive shaft of said rive, a lifting bolt having two opposing end faces and comprising a slot receiving said eccentric pin, two arms supported on said bearing sleeve, and two compression springs each supported between on of the end faces of said lifting bolt and a respective one of said arms, said lifting bolt being displaceably guided in said arms; and
   cover means for said outer casing, said over means comprises a cover and a switch cover pivotably mounted on said cover, said upper bearing web, said cover and said switch cover being superposed in a sandwich-like manner.

2. Dental instrument according to claim 1, wherein said polisher is constructed as a hook-shaped rod which at an end thereof merges into an end piece coated with diamond dust.

3. Dental instrument according to claim 1, wherein said polisher has an offset shank part of a circular cross-section and an end piece having a shaped profile provided with two side edges running together in a direction of said outer casing and having a planar surface on a side remote from said outer casing.

4. Dental instrument according to claim 1, wherein said polisher has a shank part of a circular cross-section and an end piece coated with diamond dust.

5. Dental instrument according to claim 4, wherein said end piece has an elongated, oval cross-section and is rounded at all external sides.

6. Dental instrument according to claim 1, wherein said polisher is constructed as a straight rod and includes at one end thereof a groove for receiving locking elements for mounting of said polisher in said bearing sleeve and at another end thereof an end piece coated with diamond dust.

7. Dental instrument according to claim 6, wherein said end piece is pear-shaped.

8. Dental instrument according to claim 6, wherein said end piece is spade-shaped.

9. Dental instrument for treating a tooth, comprising
   (a) a motor-driven scraping tool having a polisher for smoothing out the tooth root surfaces when reciprocating motion is imparted to said tool;
   (b) an outer casing;
   (c) an inner casing placed in said outer casing, said inner casing having an upper bearing web and a lower bearing web and a thrust ring interposed between said webs;
   (d) cover means for said outer casing, said cover means being superposed on said upper bearing web;
   (e) a bearing sleeve displaceably guided in said thrust ring and receiving and scraping tool;
   (f) a drive incorporated in said casing, having a drive shaft;
   (g) an eccentric drive operatively interconnected between said drive and said bearing sleeve so as to impart reciprocating motion to said scraping tool via said bearing sleeve, said eccentric drive having an eccentric pin connected to the drive shaft of said drive, having a lifting bolt with a slot receiving said eccentric pin and two arms supported on said bearing sleeve, each arm having a respective end face, said lifting bolt being displaceably guided in said arms, said eccentric drive further having two compression springs each supported between one of the end faces of said lifting bolt and a respective one of said arms.

10. Dental instrument according to claim 9, wherein said polisher has a shank part of a circular cross-section and an end piece coated with diamond dust.

11. Dental instrument according to claim 10, wherein said end piece has an elongated, oval cross-section and is rounded at all external sides.

12. Dental instrument according to claim 9, wherein said polisher is constructed as a straight rod and includes at one end thereof a groove for receiving locking elements for mounting of said polisher in said bearing sleeve and at another end thereof an end piece coated with diamond dust.

* * * * *